United States Patent
Berg et al.

(10) Patent No.: US 12,272,060 B2
(45) Date of Patent: *Apr. 8, 2025

(54) METHOD AND SYSTEM FOR DETERMINING CONCENTRATION OF AN ANALYTE IN A SAMPLE OF A BODILY FLUID, AND METHOD AND SYSTEM FOR GENERATING A SOFTWARE-IMPLEMENTED MODULE

(71) Applicant: Roche Diabetes Care, Inc., Indianapolis, IN (US)

(72) Inventors: Max Berg, Mannheim (DE); Fredrik Hailer, Limburgerhof (DE); Bernd Limburg, Soergenloch (DE); Daniel Sieffert, Mannheim (DE); Herbert Wieder, Lampertheim (DE); Peter Seelig, Frankfurt am Main (DE); Benhur Aysin, Fishers, IN (US); Siva Chittajallu, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,427

(22) Filed: Feb. 5, 2024

(65) Prior Publication Data

US 2024/0177304 A1 May 30, 2024

Related U.S. Application Data

(63) Continuation of application No. 17/343,513, filed on Jun. 9, 2021, now Pat. No. 11,928,814, which is a
(Continued)

(30) Foreign Application Priority Data

Dec. 21, 2018 (EP) .................................... 18215541

(51) Int. Cl.
*G06T 7/12* (2017.01)
*G01N 33/66* (2006.01)
(Continued)

(52) U.S. Cl.
CPC .......... *G06T 7/0012* (2013.01); *G01N 33/66* (2013.01); *G06T 5/50* (2013.01); *G06T 7/11* (2017.01);
(Continued)

(58) Field of Classification Search
CPC . G06T 7/0012; G06T 5/50; G06T 7/11; G06T 7/90; G06T 2207/20084;
(Continued)

(56) References Cited

U.S. PATENT DOCUMENTS 11,237,113 B2 * 2/2022 Chou ................... H04B 1/3888
2004/0092036 A1 5/2004 Chen et al.
(Continued)

FOREIGN PATENT DOCUMENTS

| JP | 2002-502045 A | 1/2002 |
| JP | 2011-515680 A1 | 5/2011 |
| WO | WO 2018/194525 A1 | 10/2018 |

OTHER PUBLICATIONS

International Search Report and Written Opinion of the International Searching Authority, PCT/EP2019/084115, Feb. 28, 2020, 13 pages.
(Continued)

*Primary Examiner* — Charlotte M Baker
(74) *Attorney, Agent, or Firm* — Bose McKinney & Evans LLP

(57) ABSTRACT

A method for generating a module configured to determine concentration of an analyte in a sample of a body fluid is disclosed. The method includes providing a first set of measurement data derived from images of one or more test
(Continued)

strips indicating a color transformation in response to a body fluid containing an analyte. The images can be recorded by multiple devices with differing cameras, software and/or hardware device configurations for image recording and image data processing. A neural network model can be generated in a machine learning process applying an artificial neural network and a module configured to determine concentration of an analyte in a second sample of a body fluid can be generated. Further, the present disclosure includes a system for generating the module as well as a method and a system for determining concentration of an analyte in a sample of a bodily fluid.

12 Claims, 15 Drawing Sheets

Related U.S. Application Data continuation of application No. PCT/EP2019/084115, filed on Dec. 9, 2019.

(60) Provisional application No. 62/777,360, filed on Dec. 10, 2018.

(51) Int. Cl.
*G06T 5/50* (2006.01)
*G06T 7/00* (2017.01)
*G06T 7/11* (2017.01)
*G06T 7/90* (2017.01)

(52) U.S. Cl.
CPC ...... *G06T 7/90* (2017.01); *G06T 2207/20084* (2013.01); *G06T 2207/30024* (2013.01)

(58) Field of Classification Search
CPC .......... G06T 2207/30024; G01N 33/66; G01N 2021/8887; G01N 21/8483; G01N 21/78; G01N 33/48; G01N 2201/1296; G16H 50/20; G06N 3/04; G06N 20/00
USPC ........................................................ 382/128
See application file for complete search history.

(56) References Cited

U.S. PATENT DOCUMENTS

| | | |
|---|---|---|
| 2006/0008923 A1 | 1/2006 | Anderson et al. |
| 2011/0250618 A1 | 10/2011 | Nelson et al. |
| 2016/0048739 A1 | 2/2016 | Burg |
| 2018/0211380 A1 | 7/2018 | Tandon et al. |

OTHER PUBLICATIONS

Parkes et al., A New Consensus Error Grid to Evaluate the Clinical Significance of Inaccuracies in the Measurement of Blood Glucose, Diabetes Care, Aug. 1, 2000, vol. 23, No. 8, pp. 1143-1148.

\* cited by examiner

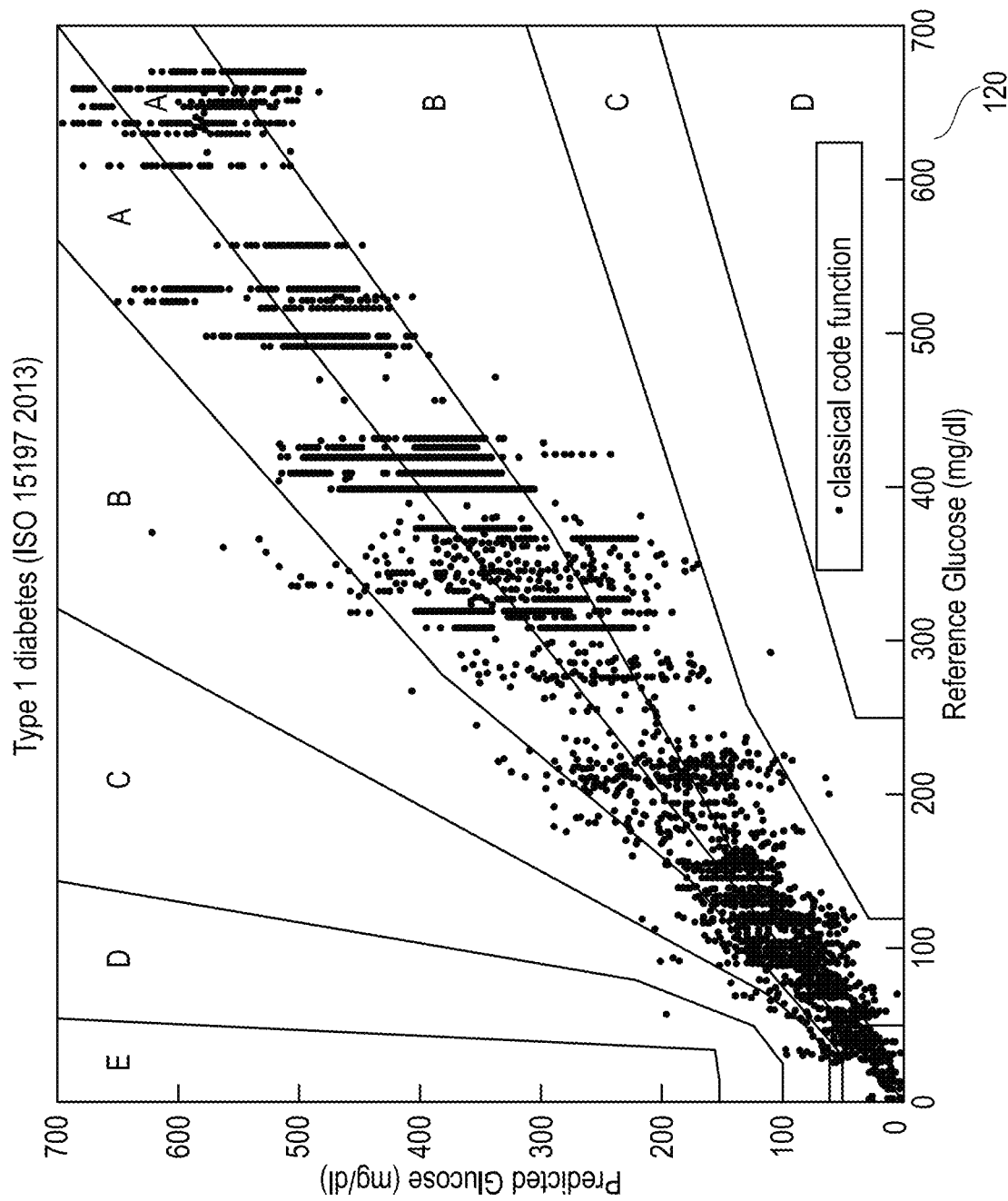

METHOD AND SYSTEM FOR DETERMINING CONCENTRATION OF AN ANALYTE IN A SAMPLE OF A BODILY FLUID, AND METHOD AND SYSTEM FOR GENERATING A SOFTWARE-IMPLEMENTED MODULE

RELATED APPLICATIONS

This application is a continuation of U.S. Utility patent application Ser. No. 17/343,513, filed Jun. 9, 2021, which claims priority to PCT/EP2019/084115, filed Dec. 9, 2019, which claims priority to U.S. Provisional Patent Application No. 62/777,360, filed Dec. 10, 2018 and EP 18 215 541.6, filed Dec. 21, 2018, the entire disclosures of all of which are hereby incorporated herein by reference.

BACKGROUND

The present disclosure relates to a method for generating a software-implemented module configured to determine concentration of an analyte in a sample of a bodily fluid and a method for determining concentration of an analyte in a sample of a bodily fluid. Further, the present disclosure relates to a system for generating a software-implemented module configured to determine concentration of an analyte in a sample of a bodily fluid and a system for determining concentration of an analyte in a sample of a bodily fluid. Also, a computer program product is disclosed.

Machine Learning (ML) is a branch of computer science that is used to derive algorithms driven by data. Instead of using explicit formulas, ML algorithms employ real-world training data to generate models that are more accurate and sophisticated than models traditionally conceived by humans. Artificial Neural Networks (ANN) belong to a branch of machine learning and rely on artificial neurons spread over multiple layers. The concept of neural networks has been around for decades, but only lately computational power caught up with the extensive computation needed in order to effectively develop neural network algorithms. Distributed computing capabilities have been enabling developers to distribute the computations over multiple units instead of using super computers. Well-known implementations for distributed computing include Apache Hadoop, Apache Spark, and MapReduce.

Neural network models are well suited for identifying patterns/non-linear relationships between an input and output when there is no or a poor direct one-to-one relationship. This is important since the accuracy of a model highly depends on how well the underlying system is characterized and how the relationship between input and output is defined.

In document US 2006/0008923 A1, systems and methods for medical diagnosis or risk assessment for a patient are provided. These systems and methods are designed to be employed at the point of care, such as in emergency rooms and operating rooms, or in any situation in which a rapid and accurate result is desired. The systems and methods process patient data, particularly data from point of care diagnostic tests or assays, including immunoassays, electrocardiograms, X-rays and other such tests, and provide an indication of a medical condition or risk or absence thereof. The systems include an instrument for reading or evaluating the test data and software for converting the data into diagnostic or risk assessment information. Patient information includes data from physical and biochemical tests, such as immunoassays, and from other procedures. The test is performed on a patient at the point of care and generates data that can be digitized, such as by an electronic reflectance or transmission reader, which generates a data signal. The signal is processed using software employing data reduction and curve fitting algorithms, or a decision support system, such as a trained neural network, or combinations thereof, for converting the signal into data, which is used to aid in diagnosis of a medical condition or determination of a risk of disease. This result may be further entered into a second decision support system, such as a neural net, for refinement or enhancement of the assessment.

Document WO 2018/0194525 A1 refers to a biochemical analyzing method for quantifying metabolites in a biological sample. The method is based on generating and learning the appearance of a test strip (dipstick) under various conditions to estimate the value/label for an unknown sample image. The method consists of two parts: a training part and a testing part. In the training part, metabolite quantities of a test strip are measured by a biochemistry analyzer. A set of images of the same test strip is captured by a device simulating various ambient lighting conditions. A machine learning model is trained using the images of the test strip and its corresponding metabolite quantities, and the learning model is transferred to a smart device. In the testing part, images of a test strip to be analyzed are captured by the smart device, and the images are processed using the learning model determined in the training part.

Document US 2018/0211380 A1 refers to a system for imaging biological samples and analyzing images of the biological samples. The system is to automatically analyze images of biological samples for classifying cells of interest using machine learning techniques. In an implementation, diseases associated with specific cell types can be diagnosed.

Document US 2016/0048739 A1 refers to a diagnostic system for biological samples. The diagnostic system includes a diagnostic instrument, and a portable electronic device. The diagnostic instrument has a reference color bar and a plurality of chemical test pads to receive a biological sample. The portable electronic device includes a digital camera to capture a digital image of the diagnostic instrument in uncontrolled lightning environments, a sensor to capture illuminance of a surface of the diagnostic instrument, a processor coupled to the digital camera and sensor to receive the digital image and the illuminance, and a storage device coupled to the processor. The storage device stores instructions for execution by the processor to process the digital image and the illuminance, to normalize colors of the plurality of chemical test pads and determine diagnostic test results in response to quantification of color changes in the chemical test pads.

SUMMARY

An improved technology for determining concentration of an analyte in a sample of a bodily fluid is disclosed.

A method for generating a software-implemented module configured to determine concentration of an analyte in a sample of a bodily fluid is also disclosed. Further, a method for determining concentration of an analyte in a sample of a bodily fluid is disclosed. A system for generating a software-implemented module configured to determine concentration of an analyte in a sample of a bodily fluid and system for determining concentration of an analyte in a sample of a bodily fluid are also provided. A computer program product is also disclosed.

According to one aspect, a method for generating a software-implemented module configured to determine concentration of an analyte in a sample of a bodily fluid is provided. The method includes, in one or more data processing devices, providing a first set of measurement data, the first set of measurement data representing first color information derived by image data processing from images for a region of interest of one or more test strips. The images are indicative of a color transformation of the region of interest in response to applying one or more first samples of a bodily fluid containing an analyte to the region of interest, and the images recorded by a plurality of devices each configured for image recording and image data processing for generating the first color information, the plurality of devices provided with different software and/or hardware device configuration applied for image recording and image data processing in the device. The method further includes, in the one or more data processing devices, generating a neural network model in a machine learning process applying an artificial neural network, including providing the neural network model, and training the neural network model by training data selected from the first set of measurement data. A software-implemented module including a first analyzing algorithm representing the neural network model is generated, wherein the software-implemented module is configured to, when loaded into a data processing device having one or more processors, determine concentration of an analyte in a second sample of a bodily fluid from analyzing a second set of measurement data indicative of second color information derived by image processing from images for a region of interest of one or more test strips, the images being indicative of a color transformation of the region of interest in response to applying the second sample of the bodily fluid containing the analyte to the region of interest.

According to one aspect, a method for determining concentration of an analyte in a sample of a bodily fluid is disclosed. The method includes, in one or more data processing devices: providing a present set of measurement data indicative of present color information derived by image processing from images for a region of interest of a present test strip or stripe, the images being indicative of a color transformation of the region of interest in response to applying a present sample of a bodily fluid containing an analyte to the region of interest; providing a software-implemented module including a first analyzing algorithm representing a neural network model generated in a machine learning process applying an artificial neural network; determining concentration of the analyte in the present sample of the bodily fluid, including analyzing the present set of measurement data by the first analyzing algorithm; and generating concentration data indicative of the concentration of the analyte in the present sample of the bodily fluid. The generating of the neural network model in the machine learning process includes providing a first set of measurement data, the first set of measurement data being indicative of first color information derived by image data processing from images for a region of interest of one or more test strips, the images being indicative of a color transformation of the region of interest in response to applying one or more first samples of a bodily fluid containing an analyte to the region of interest. The first set of measurement data are representing first color information derived from images recorded by a plurality of devices each configured for image recording and image data processing for generating the first color information, the plurality of devices being provided with a different device configuration applied for image recording and image data processing in the device. The neural network model is trained by training data selected from the first set of measurement data.

According to another aspect, a system for generating a software-implemented module configured to determine concentration of an analyte in a sample of a bodily fluid is provided. The system includes one or more data processing devices, the one or more data processing devices configured to provide a first set of measurement data, the first set of measurement data representing first color information derived by image data processing from images for a region of interest of one or more test strips. The images are indicative of a color transformation of the region of interest in response to applying one or more first samples of a bodily fluid containing an analyte to the region of interest; and the images are recorded by a plurality of devices each configured for image recording and image data processing for generating the first color information, the plurality of devices provided with different software and/or hardware device configuration applied for image recording and image data processing in the device. The one or more data processing devices can be configured to generate a neural network model in a machine learning process applying an artificial neural network, including providing the neural network model, and training the neural network model by training data selected from the first set of measurement data. Further, the one or more data processing devices can be configured to generate a software-implemented module including a first analyzing algorithm representing the neural network model, wherein the software-implemented module is configured to, when loaded into a data processing device having one or more processors, determine concentration of an analyte in a second sample of a bodily fluid from analyzing a second set of measurement data indicative of second color information derived by image processing from images for a region of interest of one or more test strips, the images being indicative of a color transformation of the region of interest in response to applying the second sample of the bodily fluid containing the analyte to the region of interest.

According to still another aspect, a system for determining concentration of an analyte in a sample of a bodily fluid is disclosed. The system includes one or more data processing devices, the one or more data processing devices can be configured to: provide a present set of measurement data indicative of present color information derived by image processing from images for a region of interest of a present test strip, the images being indicative of a color transformation of the region of interest in response to applying a present sample of a bodily fluid containing an analyte to the region of interest; provide a software-implemented module including a first analyzing algorithm representing a neural network model generated in a machine learning process applying an artificial neural network; determine concentration of the analyte in the present sample of the bodily fluid, including analyzing the present set of measurement data by the first analyzing algorithm; and generate concentration data indicative of the concentration of the analyte in the present sample of the bodily fluid. The generating of the neural network model in the machine learning process includes providing a first set of measurement data, the first set of measurement data being indicative of first color information derived by image data processing from images for a region of interest of one or more test strips, the images being indicative of a color transformation of the region of interest in response to applying one or more first samples of a bodily fluid containing an analyte to the region of interest.

The first set of measurement data represents first color information derived from images recorded by a plurality of devices each configured for image recording and image data processing for generating the first color information, the plurality of devices being provided with a different device configuration applied for image recording and image data processing in the device. The neural network model is trained by training data selected from the first set of measurement data.

Further, a computer program product, including program code configured to, when loaded into a computer having one or more processors, perform the above methods is disclosed.

The neural network model generated in the machine learning process allows for improved determination of the concentration of the analyte in the (present) sample of the bodily fluid. Having the neural network model generated based on the first set of measurement data representing first color information derived from images recorded by the plurality of different devices each configured for image recording and image data processing for generating the first color information provides for a neural network model which, after training and testing, can be applied or implemented on different devices for determining concentration of an analyte in a sample of a bodily fluid, the different devices having different device configurations applied for image recording and image data processing in the respective device.

The neural network model generated before is applied for analyzing the present or second set of measurement data indicative of present/second color information derived by image processing from images for a region of interest of the present/second test strip, the images being indicative of a color transformation of the region of interest in response to applying a present/second sample of a bodily fluid of a patient, the sample containing an analyte to the region of interest. In such process, the analyte concentration is determined for the patient for whom the sample is provided.

The method may include the plurality of devices having at least one of different camera devices and different image processing software applied for image recording and image data processing.

The images recorded may include images recorded with different optical image recording conditions.

The method may further include the following: providing a second analyzing algorithm, the second analyzing algorithm being different from the first analyzing algorithm; and determining, for the concentration of the analyte in the present sample of the bodily fluid, a first estimation value by analyzing the present set of measurement data by means of the second analyzing algorithm. The second analyzing algorithm may be a non-machine learning based algorithm such as parametric multivariate linear regression. Such non-machine learning based algorithm may also be referred to as a traditional algorithm for determining analyte concentration. The first estimation value for the analyte concentration may provide for an input to the (further) analysis by means of the neural network model. Alternatively, the result for the concentration derived from the non-machine learning based algorithm may be applied in a failsafe test for the analyte concentration values determined by applying the neural network model.

The determining may include determining a target range for the concentration of the analyte in the present sample of the bodily fluid. Instead of determining actual values for the analyte concentration or in addition to such determination, the target range for the analyte concentration values may be determined.

The determining may include determining an averaged concentration by averaging the first estimation value and a concentration value provided by the analyzing of the present set of measurement data by the first analyzing algorithm. Results from the neural network model analysis and the analysis based on the traditional algorithm are combined by determining averaged values.

In another embodiment, the determining may include determining concentration of blood glucose in the second sample.

At least one of the first, second and present set of measurement data may be representing first, second, and present color information, respectively, derived by image processing from images recorded over a measurement period of time for the region of interest of the one or more test strips, consecutive images recorded with a time interval from about 0.1 to about 1.5 s.

The images from which the first set of measurement data is derived may include images of the region of interest prior to applying the one or more first samples of the bodily fluid to the region of interest of the one or more test strips. Similarly, in addition or alternatively, the images from which the present set of measurement data is derived may include images of the region of interest prior to applying the present sample of the bodily fluid to the region of interest of the present test strip.

In an example, it may be provided that the measurement data are divided into a training data set, a validation data set, and a test data set. For example, about 60% of the measurement data may be used for training (training data set), about 20% for validation (validation data set), and about 20% for testing (test data set). Cross validation techniques such as leave-p-out cross validation or k-fold cross validation can be employed. The training data set may be created by using stratified random sampling of the measurement data. Stratification may be conducted based on at least one of type of device applied for gathering measurement data and type of experiment applied while collecting the measurement data. The measurement data are divided into separate subpopulations (strata), wherein each stratum may correspond to a different device type and/or different type of experiment. Subsequently, data may be sampled separately for each stratum and then merged in order to create the training data set. Doing so can be applied for assuring that the training data represent essentially the full population of device types and/or experiment types. The validation data set(s) and test data set(s) can be created analogously.

The embodiments disclosed above with respect to at least one of the methods may apply to one or both systems mutatis mutandis.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 12A shows a Parkes error grid for a traditional algorithm.

DESCRIPTION

Figure 1:
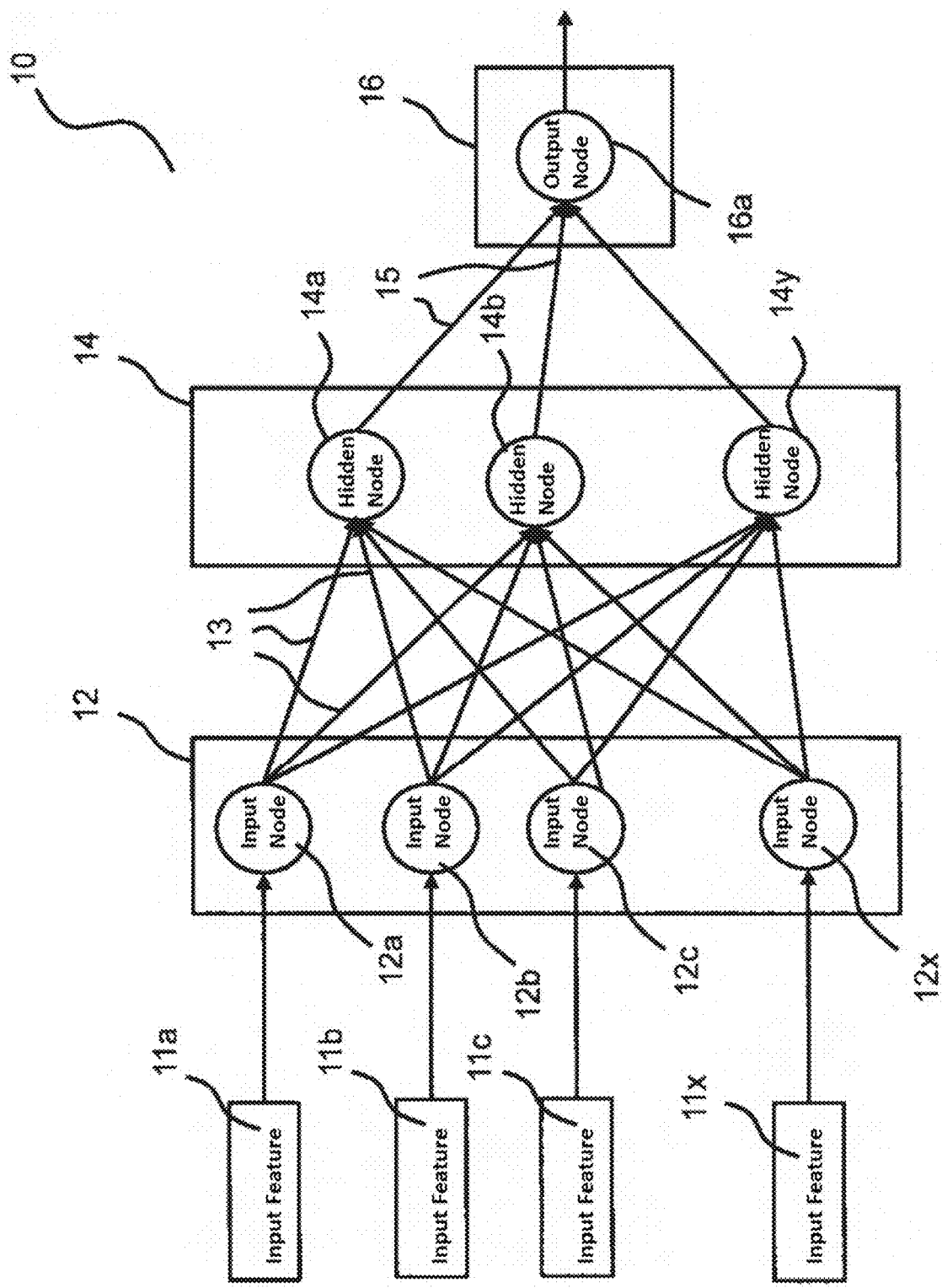
FIG. 1 shows a graphical representation of a feed forward artificial neural network (ANN).

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Following, embodiments for a method for generating a software-implemented module configured to determine concentration of an analyte in a sample of a bodily fluid are disclosed in further detail. After the software-implemented module has been generated, in a further method, it can be used on different devices such as mobile devices for analyzing experimental results for determining concentration of an analyte in a sample of a bodily fluid applied to a test strip for which a test region will show a color change in response to applying the sample to the test region on the strip.

The method for generating a software-implemented module is conducted in one or more data processing devices. A first set of measurement data is provided, the first set of measurement data representing first color information derived by image data processing from images for a region of interest of one or more test strips. For example, blood samples may be applied to the test strips, which in response show color change of the region of interest (test region). Such color change may be dependent on a blood glucose concentration in the samples dosed to the test region. The images captured for the region of interest are indicative of a color transformation of the region of interest in response to applying one or more first samples of a bodily fluid containing an analyte to the region of interest. The images are recorded by a plurality of devices, such as mobile devices, e.g., mobile phones or tablet computers. Each device is configured for image recording and image data processing for generating the first color information, the plurality of devices are provided with different software and/or hardware device configurations applied for image recording and image data processing in the device. For example, the devices may be provided with different types of cameras used for capturing the images. Also, different software configuration may be provided for the devices, specifically different software applications applied in the devices for processing the images captured.

A neural network model is generated in a machine learning process applying an artificial neural network, including providing the neural network model, and training the neural network model by training data selected from the first set of measurement data. The software-implemented module is provided including a first analyzing algorithm representing the neural network model. The software-implemented module is configured to, when loaded into a data processing device having one or more processors, determine concentration of an analyte in a second sample of a bodily fluid from analyzing a second set of measurement data indicative of second color information derived by image processing from images for a region of interest of one or more test strips, the images being indicative of a color transformation of the region of interest in response to applying the second sample of the bodily fluid containing the analyte to the region of interest. Thus, after the neural network model has been generated it is to be applied for analyzing the results for the second sample, which may also be referred to as a present sample and which is a sample of a bodily fluid to be determined by using the neural network model after its generation as explained in further detail in the following. A software application including the software-implemented module is to be loaded to the analysis device such as a mobile phone or other mobile device. The test strip analysis is conducted by running the software application for determining the concentration of the analyte.

FIG. 1 shows a schematic graphical representation of a feed forward artificial neural network (ANN) 10. In a typical feed forward ANN, information flows one way. Input features 11a, 11b, 11c, . . . , 11x are fed to nodes (or artificial neurons) 12a, 12b, 12c, . . . , 12x of an input layer 12. The number of the nodes 12a, 12b, 12c, . . . , 12x should ideally be equal to the number of features in the underlying dataset. The input layer 12 simply receives the input features 11a, 11b, 11c, . . . , 11x and passes the input features 11a, 11b, 11c, . . . , 11x via connections 13 to a hidden layer 14.

The hidden layer 14 includes nodes 14a, 14b, . . . , 14y. The number of nodes of the hidden layer 14 depends on the number of nodes of the input layer 12 and the output layer 16. The number of nodes of the input layer 12 and the hidden layer 14 can be equal or unequal. In each node 14a, 14b, . . . , 14y, a transformation is applied to its respective input. Subsequently, the transformed values are passed on via connections 15 to the output layer 16. As the ANN 10 is trained, nodes 12a, 12b, 12c, . . . , 12x, 14a, 14b, . . . , 14y that provide higher predictive value are weighted to a higher extent. The respective connections 13, 15 receive a higher weight.

The output layer 16 provides the information that is desired for solving the underlying problem. The number of its nodes 16a depends on the problem at hand. If the problem is to, e.g., classify an object into one of four classes, then the output layer 16 will consist of four nodes (not shown). If the problem amounts to a regression, then the output layer 16 will consist of a single node 16a.

Figure 2:
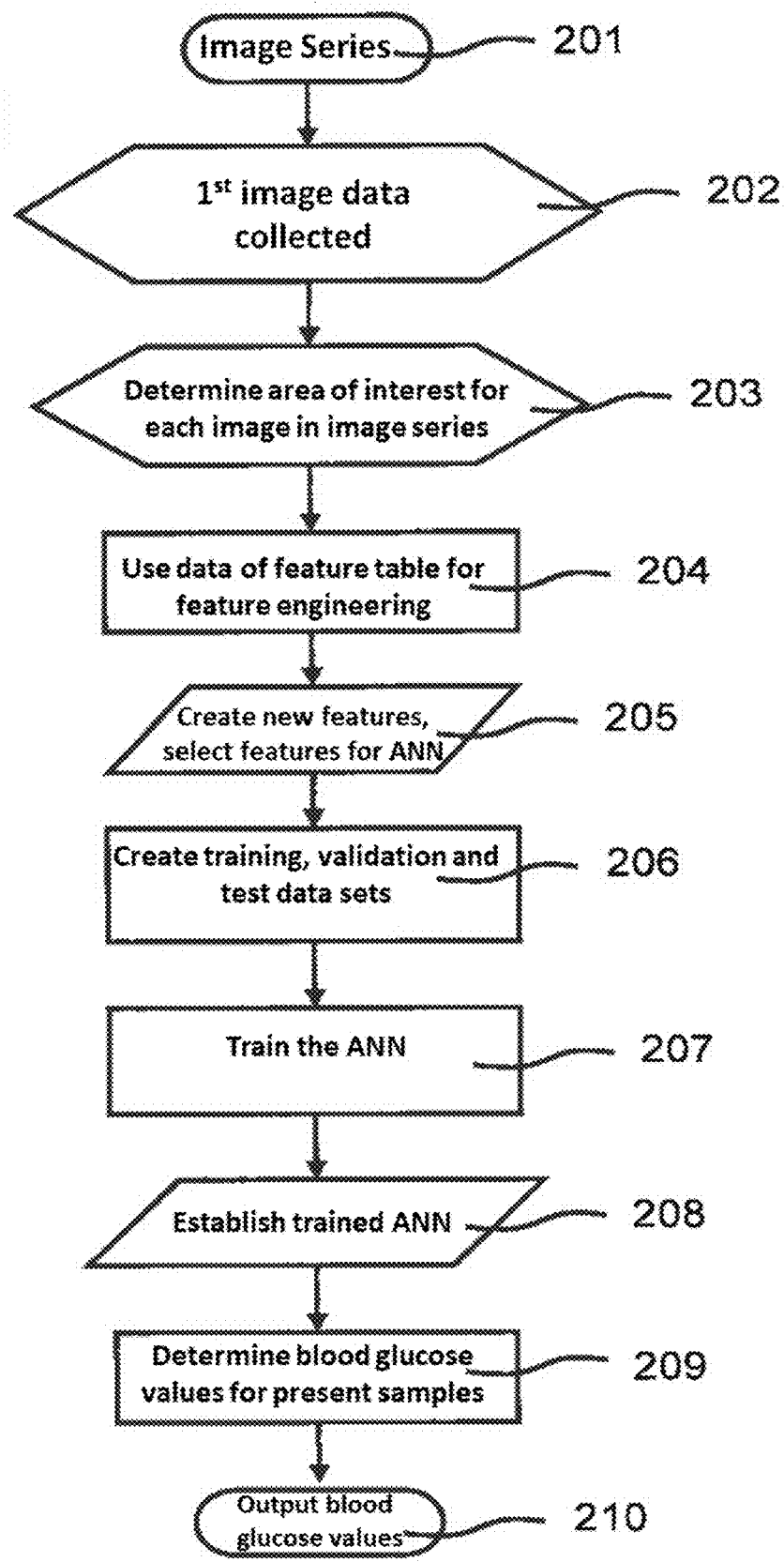
FIG. 2 shows a graphical representation of a method for predicting blood glucose values based on the color change of a dosed test strip.

In the following, examples are disclosed for applying ANNs for determining concentration of an analyte in a sample of a bodily fluid from measurements based on the color change in a test region of a test strip in response to applying the sample of the bodily fluid. For example, a blood glucose level may be determined. FIG. 2 schematically illustrates the steps for an example of the method.

In the course of the measurement, image series 201 of test strips are captured in a first image data collection step 202 using different devices each device being configured for taking images and processing image data. The devices may be mobile devices such as cell or mobile phone types or tablet computers.

For taking the images, a sample of a bodily fluid, e.g., a blood sample, is applied to a test region of the test strip. In response to the application of the sample, the test region will show color change which is to be detected by the taking of the image(s). The images are to be processed in an analyzing process for determining concentration of an analyte in the sample of the bodily fluid, such as a blood glucose level.

While the images are taken for determining the sample of the bodily fluid, different measurement conditions may be present for capturing the images by combinations of, e.g., different temperatures, relative humidity values, illumination values, and/or hematocrit. Other values may also be used. In an example, with respect to different climate conditions, temperature values from 5° C. to 30° C. in steps of, for example, 5° C., and relative humidity values from 15% to 85% in steps of, for example, 10% can be applied. It may be provided that each of the relative humidity values is combined with each of the temperature values in order to form the set of different climate conditions. Alternatively, only certain relative humidity values may be combined with each of the temperature values since certain relative humidity/temperature combinations are less relevant.

The following measurement conditions may be applied in the data set for temperature and humidity in climate studies:

| Temp (° C.) | rel. Humidity (%) |
|---|---|
| 5 | 45 |
| 10 | 15 |
| 10 | 45 |
| 10 | 85 |
| 15 | 45 |
| 25 | 45 |
| 30 | 45 |
| 30 | 85 |

For each test strip, an image series 201 is captured for a measurement period of time. For example, for about 40 seconds an image 30 of the test strip is captured every half second (see FIG. 3 for a graphical representation of image 30). Each image series 201 per test strip starts with an image of a blank test strip (a test strip without applied blood dose or sample). The subsequent images 30 are captured after applying the blood sample. Thus, the change of color of the test strip is completely captured within each image series 201. The image series 201 may be saved into a database. An additional time delay between capturing the first and the second image enabling a user to apply a blood dose to the test strip may be provided.

The images can be captured with a plurality of different cell or mobile phones, each cell phone being provided with an individual camera device and software configuration of image processing parameters RGGB, a color transformation matrix and a tone map curve for capturing the images and processing image data.

The images taken in the measurements provide for (measured) image data representing color information with respect to the color change of the test region in response to applying the sample(s) of the bodily fluid containing the analyte for which concentration needs to be determined. Following, the image data are used for generating a software-implemented module configured to determine concentration of the analyte in a present sample. An ANN is provided and trained based on a training data set taken from the measured image data.

Figure 3:
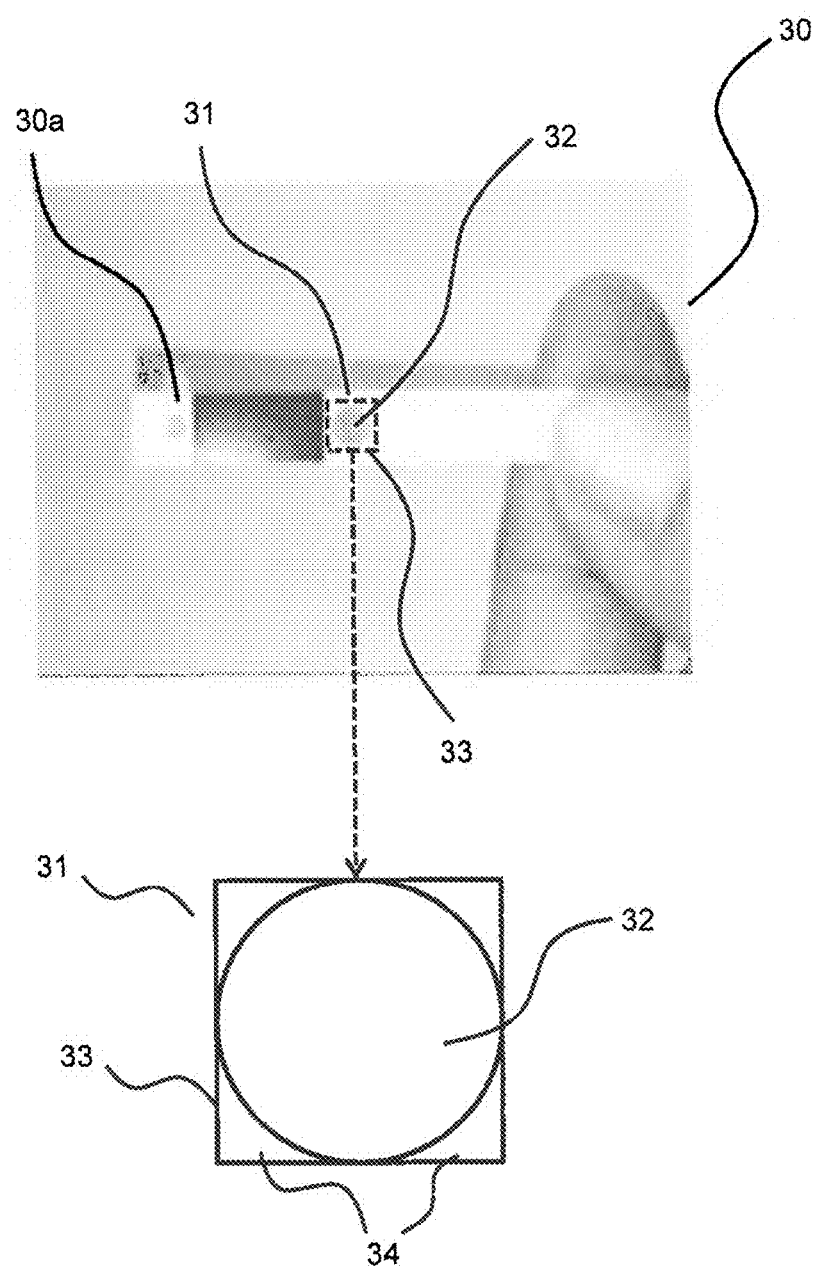
FIG. 3 shows a graphical representation of an image of a test strip.

In the next step 203, referring to FIGS. 2 and 3, the image data derived from the image series 201 which may be saved in a database are processed in order to determine an area of interest 31 for each image 30 of the image series 201. The area of interest 31 consists of the part of the image showing the applied sample of the bodily fluid (e.g., blood sample) on a test strip 30a (target field 32) and a square 33 around the target field 32. The space outside the target field 32 and inside the square 33 consisting of four segments is called white field 34. The area of interest (test region) 31 is detected by image processing software by capturing pixel color values for the target field 32 and the white field 34. Each pixel color may, E.g., be RGB encoded. Alternative color spaces and color models such as CIE L*a*b*, CIE 1931 XYZ, CMYK, and HSV can also be employed for encoding the pixel colors. The use of alternative color spaces and color transformations into the alternative color spaces can enhance signal quality, leading to simpler and/or more accurate prediction algorithms.

The raw pixel data can be transformed in order to improve signal precision. The following types of color transformations, or combinations thereof, can be employed:

Means of the raw R, G, and B channel are calculated from the target field 32 where blood is applied;
1 R and G channels are normalized by B from the target field 32 (the normalization is performed by dividing each of the R and G channel value by the corresponding B value);
a Delta between R and B channels and a Delta between G and B channels from the target field 32 are calculated;
the R,G,B channels from the target field 32 are normalized by the R,G,B channels from the white field 34;
a ratio between target white normalized R,G,B channels of the target field 32 and white normalized R,G,B channels of a reference field is calculated.

This list of color transformations is not exhaustive. Further color transformations for different features can be provided.

For the devices applied for image taking, e.g., a plurality of cell or mobile phones, different methods for calibrating can be employed. Differences in color adjustment schemes among different cell phone types will result in divergent glucose prediction performance if left uncorrected. A variety of approaches can be used in order to generate cellphone type specific calibration curves that will standardize the outputs to a common reference scale. On the one hand, offline calibration can be performed using color reference cards including regions of known chromaticity. Such offline calibration does not need to be carried out before each measurement. It can be provided that the offline calibration is performed once, before any measurement is carried out by a user. Alternatively, the offline calibration can be carried out at periodic time intervals. On the other hand, online calibration using color references can be employed. For this, reference card images are captured along with a test field at a pre-specified time after the test strip has been dosed. Images of the test strip are captured before dosing and after dosing. The test strip may additionally have pre-printed reference fields for online calibration.

Once the target field 32 is located, RGB pixels values from a region within the target field 32, e.g., a circle with a slightly smaller radius inside the target field 32, are extracted and averaged for each channel, yielding average values for each of the R, G and B channel. Thus, averaging unwanted pixels at the boundary of the target field 32 can be avoided.

Subsequently, the average values for each color channel are saved into a data table together with further relevant data such as a reference glucose value, an image ID, a study name, error codes, study related information such as temperature, humidity, hematocrit, or device model numbers. The data table can, e.g., be saved as comma separated value (csv) file or MATLAB mat file for further processing.

For specific modeling purposes, not every column of the data table is relevant. Therefore, a smaller table, the feature table, is generated from the data table by only including the columns that are required for modeling. An exemplary table with four rows for the feature table is depicted in table 1.

necessary for modeling. It may be sufficient or desirable to employ the data from the final image and from 10 to 19 images preceding the final image for the modeling. In the final images, the slope of R or G channels is close to zero, i.e., color kinetics are stabilized at a certain time after dosing and colors do not change or change only minimally from that point on. Taking images with stationary color kinetics can increase comparability of the images.

Further referring to FIG. 2, in step 204, the data of the feature table are used for feature engineering. One of the aspects of the modeling is to select the proper features for a model. Since the goal is to predict blood glucose values, using features that have a strong correlation with reference blood glucose values is expected to result in better models. The reference blood glucose values have been determined with established blood glucose measuring systems. The linear RGB channels exhibit a certain degree of correlation with the reference glucose values. However, results can still

TABLE 1

Exemplary depiction of a feature table.

| sequ. no. | observ. no. | BlankimageName | finalimageName | tfRlin | tfGlin | tfBlin |
|---|---|---|---|---|---|---|
| 1 | 1 | R5-W2-07_*_image | R5-W2-07_*_image | 129.5 | 126.74 | 72.89 |
| 2 | 1 | R5-W2-07_*_image | R5-W2-07_*_image | 129.6 | 126.68 | 73.58 |
| 3 | 1 | R5-W2-07_*_image | R5-W2-07_*_image | 129.8 | 126.92 | 73.35 |
| 4 | 1 | R5-W2-07_*_image | R5-W2-07_*_image | 129.9 | 126.95 | 73.74 |

| sequ. no. | wfRlin | wfGlin | wfBlin | glcCode Value Cont | blank ValueRtf |
|---|---|---|---|---|---|
| 1 | 207.35 | 206.164 | 202.28 | 10.46475029 | 145.2584534 |
| 2 | 207.16 | 206.037 | 201.79 | 10.11334229 | 145.2584534 |
| 3 | 207.63 | 206.186 | 202.02 | 10.42901993 | 145.2584534 |
| 4 | 207.38 | 206.262 | 202.08 | 9.864500046 | 145.2584534 |

| sequ. no. | blank ValueGtf | blank ValueBtf | blank ValueRwf | blank ValueGwf | blank ValueBwf |
|---|---|---|---|---|---|
| 1 | 143.0743256 | 73.74324036 | 209.0067902 | 207.8676453 | 204.3337097 |
| 2 | 143.0743256 | 73.74324036 | 209.0067902 | 207.8676453 | 204.3337097 |
| 3 | 143.0743256 | 73.74324036 | 209.0067902 | 207.8676453 | 204.3337097 |
| 4 | 143.0743256 | 73.74324036 | 209.0067902 | 207.8676453 | 204.3337097 |

The feature table includes linear average RGB channel values for both the target field (tfRlin, tfGlin, tfBlin) and the white field (wfRlin, wfGlin, wfBlin). The linearization is achieved by setting the tone map curve of a smartphone to a straight 1:1 line. The linearization is necessary for handling different default tone map curves in different smartphone types. Without setting the tone map curve, the relationship between the values would be artificially nonlinear due to the default tone map curves being nonlinear. The averaging is performed for each RGB channel separately by taking the arithmetic average of the channel values of the respective region (target field or white field).

The feature table further includes linear average RGB channel values for the target field (blank ValueRtf blank ValueGtf, blank ValueBtf) and the white field (blank ValueRwf, blank ValueRwf, blank ValueRwf) before dosing.

Data can be assessed as invalid if it is determined that the data is very (partly) overexposed, inhomogeneous, included too few pixels, the corresponding image was not sharp enough, or a combination thereof. The invalid data can be removed from the feature table. The feature table does not include information from all the images of the same measurement. In general, for each image series 201, roughly 80 images 30 are captured, but not all the images 30 are be improved by creating new features having a stronger correlation with the reference glucose values. Creating such new features may moreover be beneficial in that dependencies could be decreased with respect to different cell phone types and measurement conditions such as climate conditions or illumination conditions.

Figure 4:
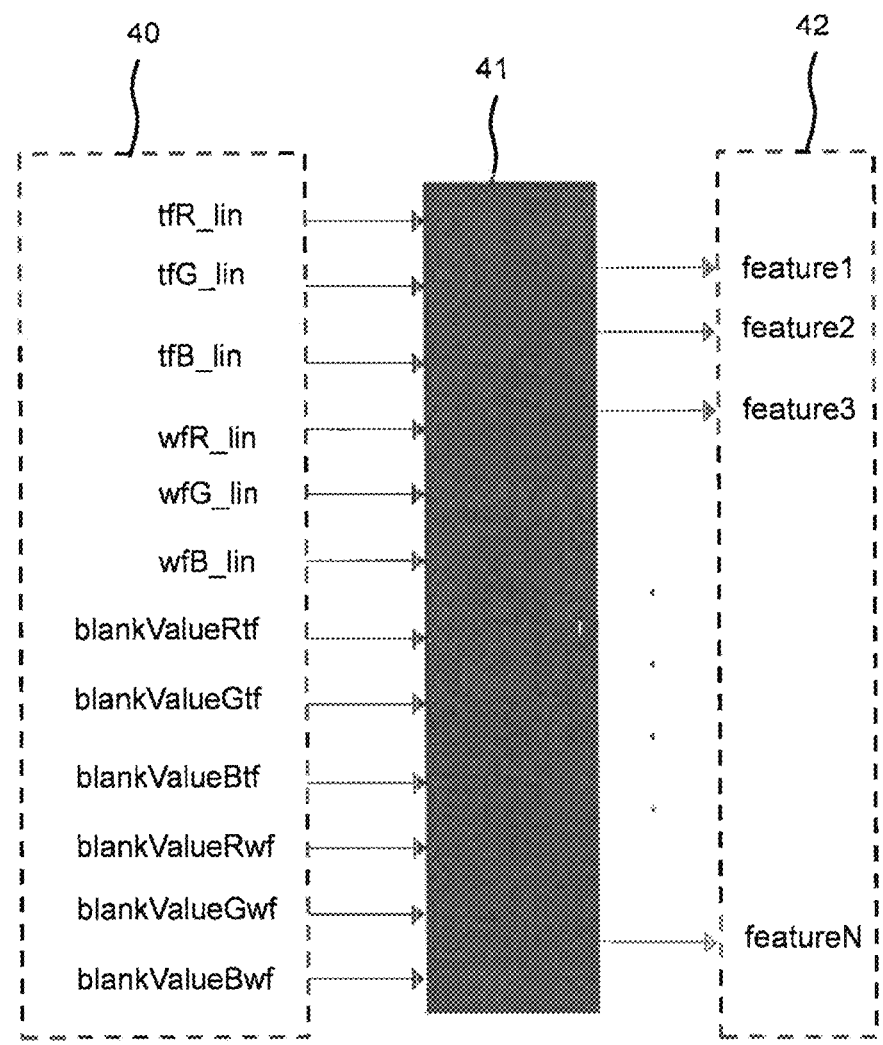
FIG. 4 shows a graphical representation of the process of creating new features out of features from the feature table by applying a feature transformation.

In this regard, FIG. 4 shows a graphical representation of the process of creating new features 42 out of features 40 from the feature table by applying a feature transformation 41 such as a color transformation to the features 40. The features 40 may include the linear average RGB channel values for the target field (tfRlin, tfGlin, tfBlin), and/or the white field (wfRlin, wfGlin, wfBlin), and/or the RGB channel values before dosing (blank ValueRtf blank ValueGtf, blank ValueBtf), (blank ValueRwf, blank ValueRwf, blank ValucRwf).

Figure 5A:
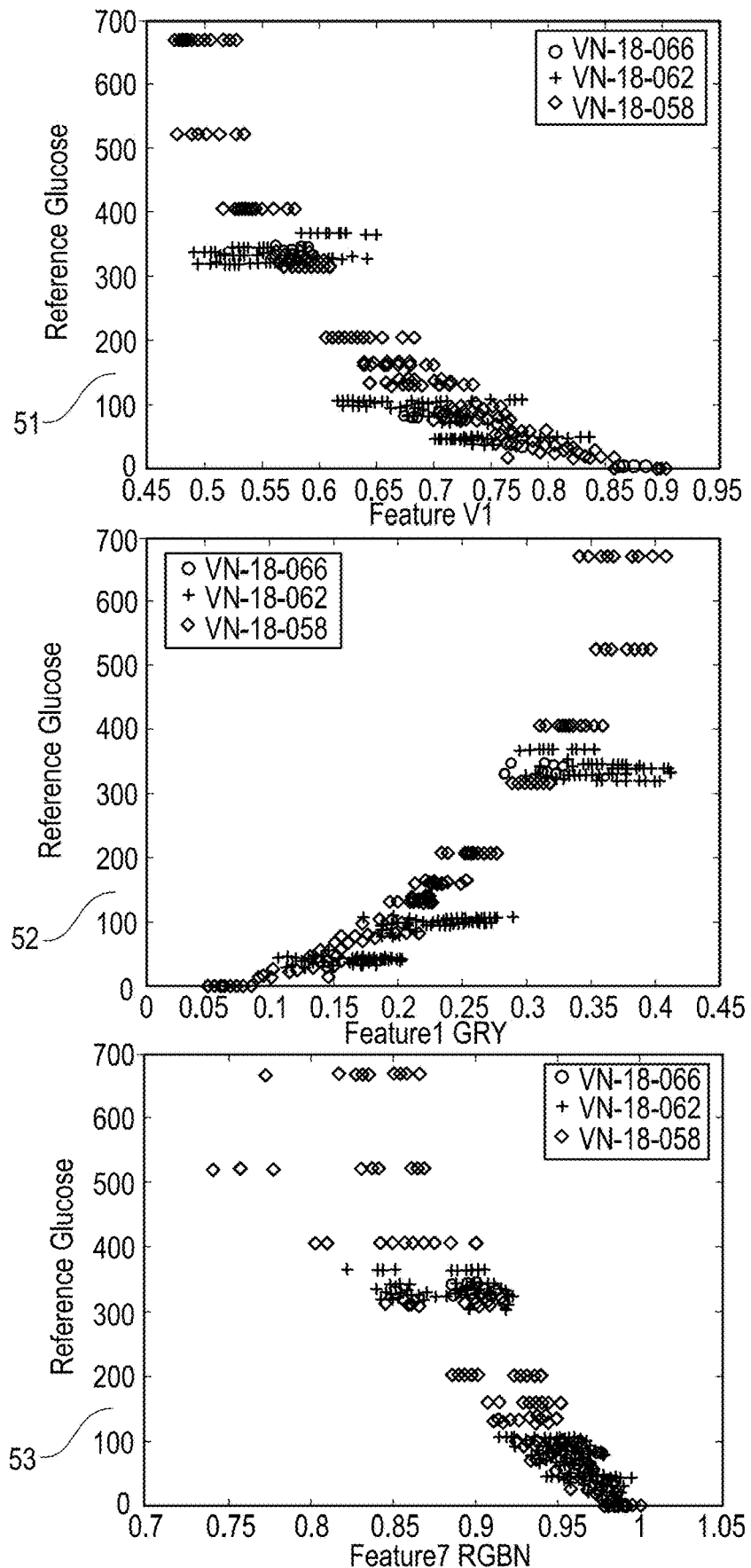
FIG. 5A shows a graphical representation of the correlation behavior of exemplary new features.
Figure 5B:
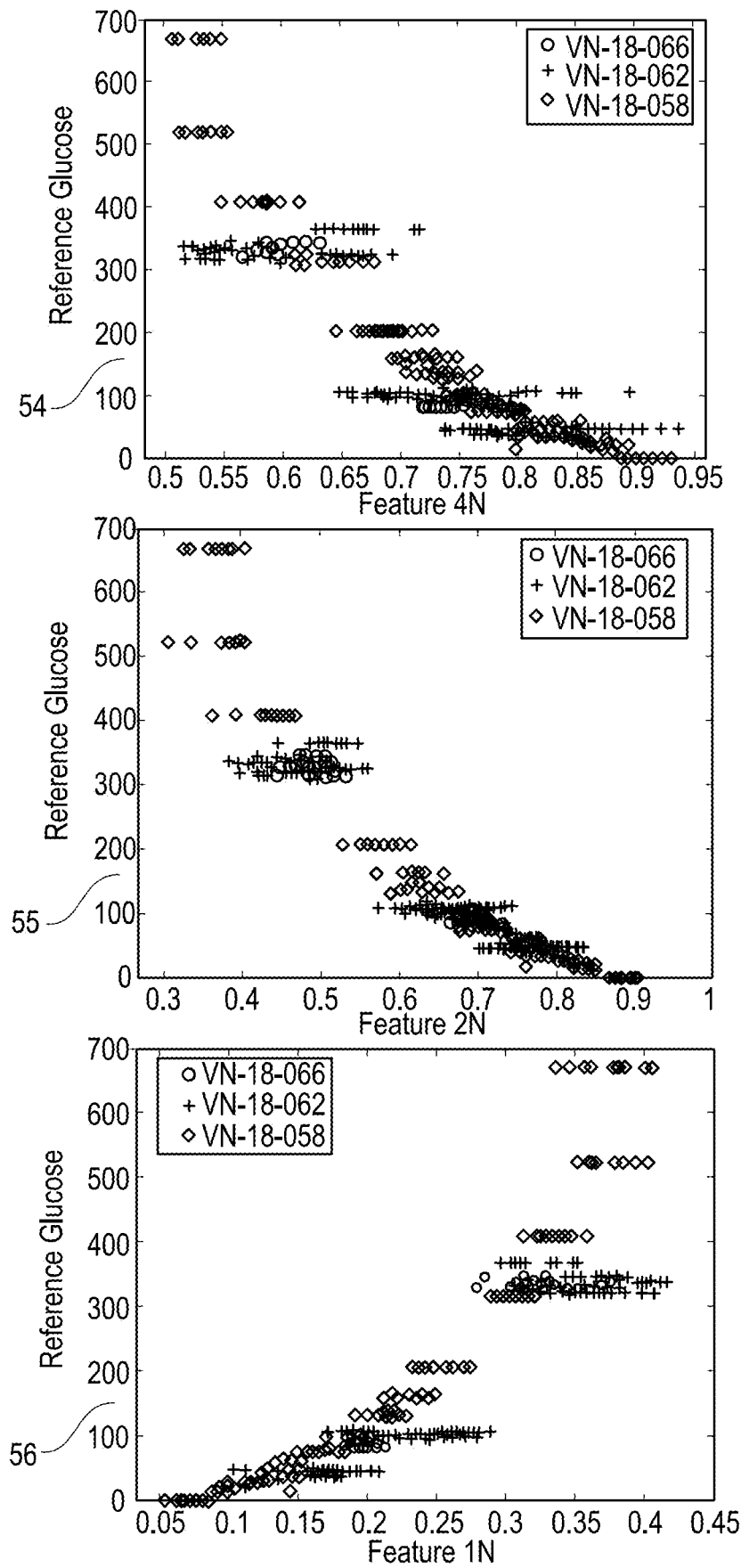
FIG. 5B shows a further graphical representation of the correlation behavior of exemplary new features.

In FIGS. 5*a* and 5*b*, depictions of the correlation behavior of exemplary new features 42 created by the feature transformation 41 of the features 40 are shown. Graphs 51 to 56 each display the correlation behavior of one of the new features 42 (x-axes) with the reference blood glucose values (y-axes). The feature "GRY" as in graph 52 refers to grayscale color values. The suffix "N" in certain features refers to normalization. In particular, "RGBN" as in graph 53 means "RGB color normalized". Different markers (○, +, ◊) correspond to different experiment types. The depicted new features 42 exhibit a stronger correlation with reference glucose values than just raw RGB values.

Figure 5C:
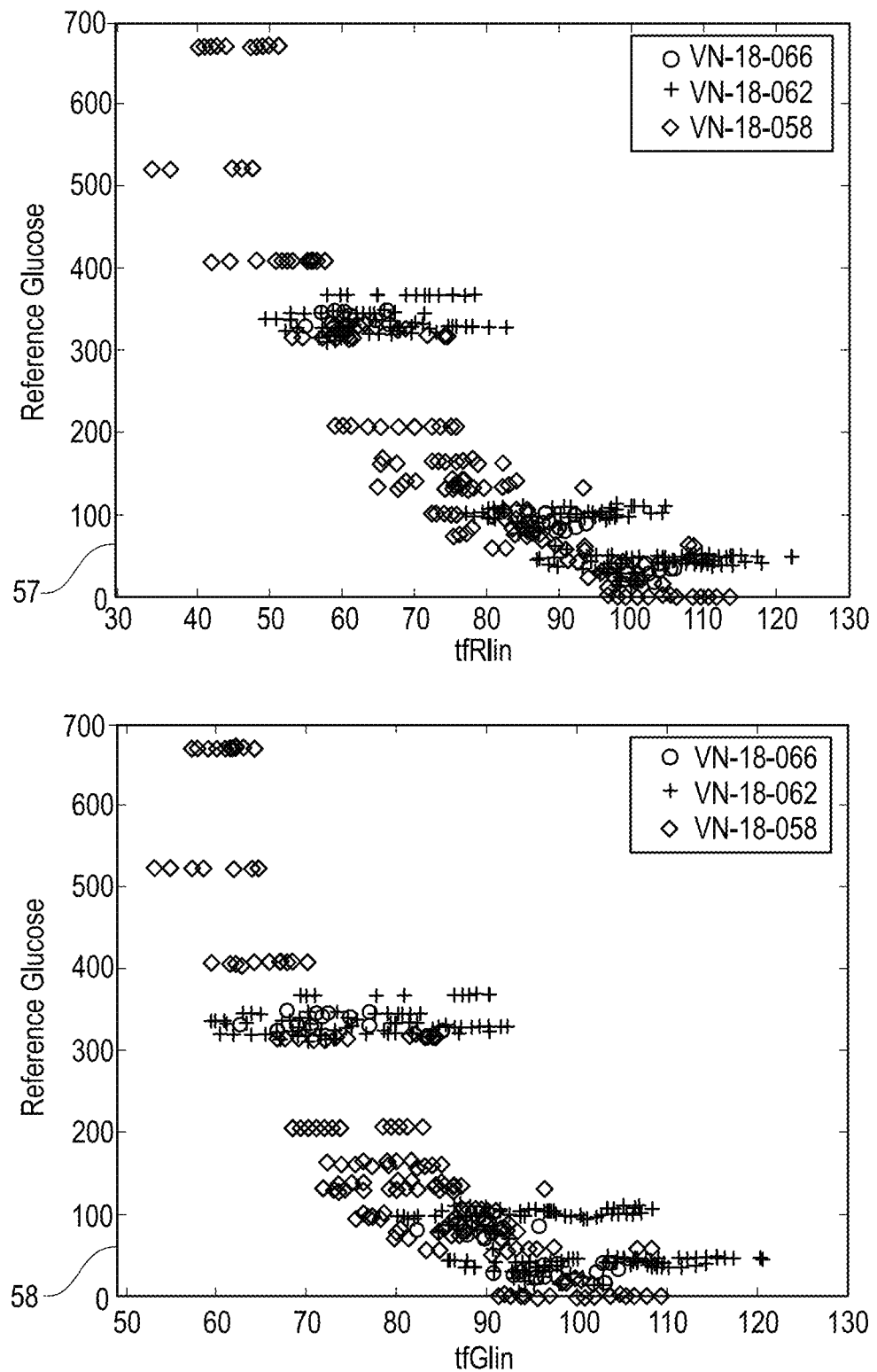
FIG. 5C shows a further graphical representation of the correlation behavior of exemplary new features.

In contrast, FIG. 5c shows depictions of the correlation behavior of raw RGB channel values with the reference blood glucose values. Graph 57 shows the linear average R channel value for the target field tfRlin. Graph 58 shows the linear average G channel value for the target field tfGlin. The graphs 57 and 58 show a larger scattering of the values and hence a weaker correlation with the reference blood glucose values than the new features 42 depicted in FIGS. 5a and 5b.

Referring again to FIG. 2, in a subsequent step 206, training, validation, and test sets can be created from the data in the feature table before an ANN model can be trained. It may be provided that the data are divided into a training, a validation, and a test set. 60% of the data are used for training, 20% for validation, and 20% for testing. Cross validation techniques such as leave-p-out cross validation or k-fold cross validation can also be employed. The training set is created using stratified random sampling of the data. Stratification can be conducted based on smartphone types and experiment types. As in, the data can be divided into separate subpopulations (strata), wherein each stratum corresponds to a different smartphone type and experiment type. Subsequently, data can be sampled separately for each stratum and then merged in order to create the training data. Doing so assures that the training data still represent the full population of smartphone and experiment types. The validation sets and test sets can be created analogously.

The validation set is used in order to prevent overtraining/overfitting, while the test set is used for an independent evaluation of the model during the training. A column is added to an input dataset to indicate which data is used for training, testing and validation. The added column is to identify proper subsets when training the ANN.

Figure 6:
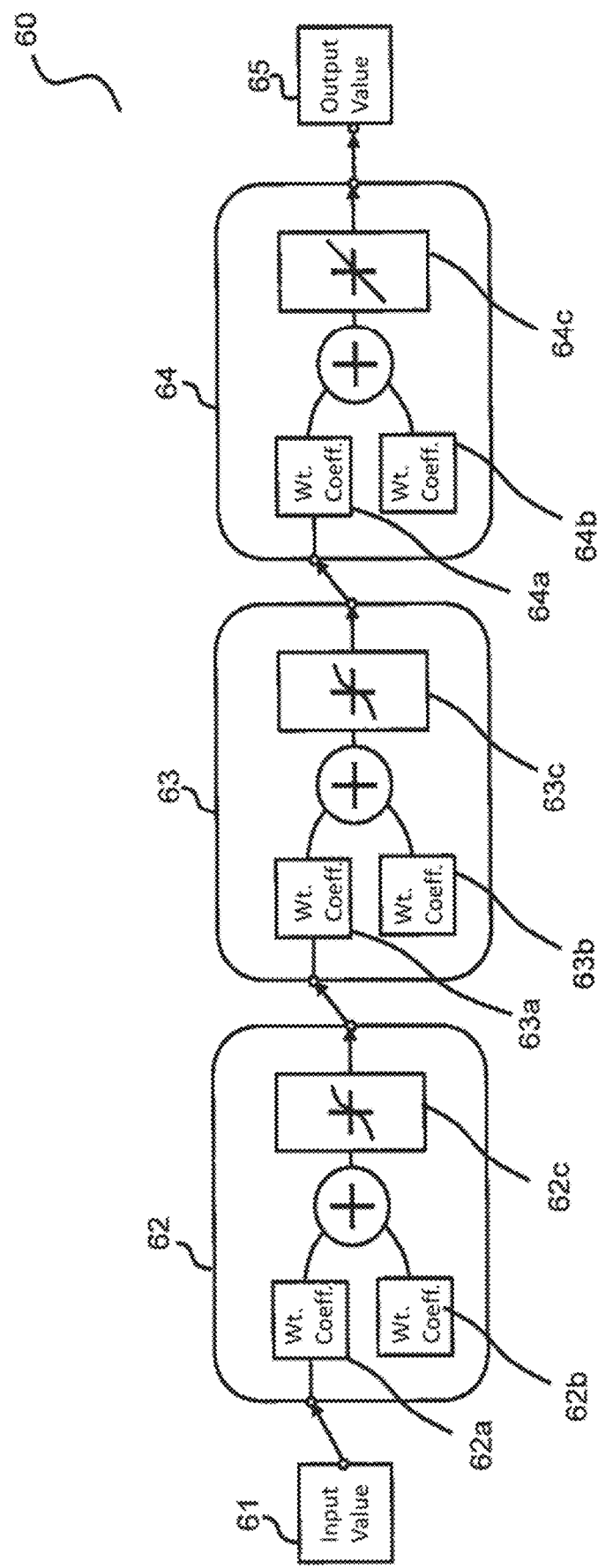
FIG. 6 shows a graphical representation of an architecture of an ANN model to be trained.

In step 207, the ANN is trained. The ANN is trained with different measurement conditions such that the different measurement conditions are represented in the training set and can be included in the model. It can also be provided that different smartphone types are included in the modelling. The training of the ANN can be performed in numerical computing environments such as MATLAB. For increased performance, compiled programming languages can also be employed. FIG. 6 shows a graphical representation of an exemplary architecture of an ANN model 60 to be trained. The architecture in FIG. 6 includes two hidden layers 62, 63. Alternatively, a single hidden layer of more than two hidden layers can be employed (not shown) depending on the complexity of the problem. Input values 61 are passed to the hidden layer 62. The output of the hidden layer 62 is passed to the hidden layer 63. The output of the hidden layer 63 in turn is passed to an output layer 64, resulting in an output value 65. The output value 65 corresponds to a predicted blood glucose value. Weight coefficients 62a, 62b, 63a, 63b, 64a, and 64b are optimized during the training for the proper blood glucose model.

Regularization methods such as early stopping can be used to prevent overtraining. For example, it can be provided that a maximum of 12 iterations is allowed for training the model 60. The maximum number of epochs can be set to 1000, for example. Multiple models 60 with different initialization points are trained and their performance metrics saved into a table file, such as a csv file, for later model selection. Once all the models 60 are created and performance metrics are evaluated, a best performing model is selected as the final trained model.

Referring back to FIG. 2, in step 208, the trained model is established using a neural network formula consisting of linear combination of hyperbolic tangents of features with optimized coefficients obtained from the trained ANN. By use of the trained neural network model, blood glucose values are determined (step 209). Subsequently, the determined blood glucose values are output for further processing (step 210).

Figure 7:
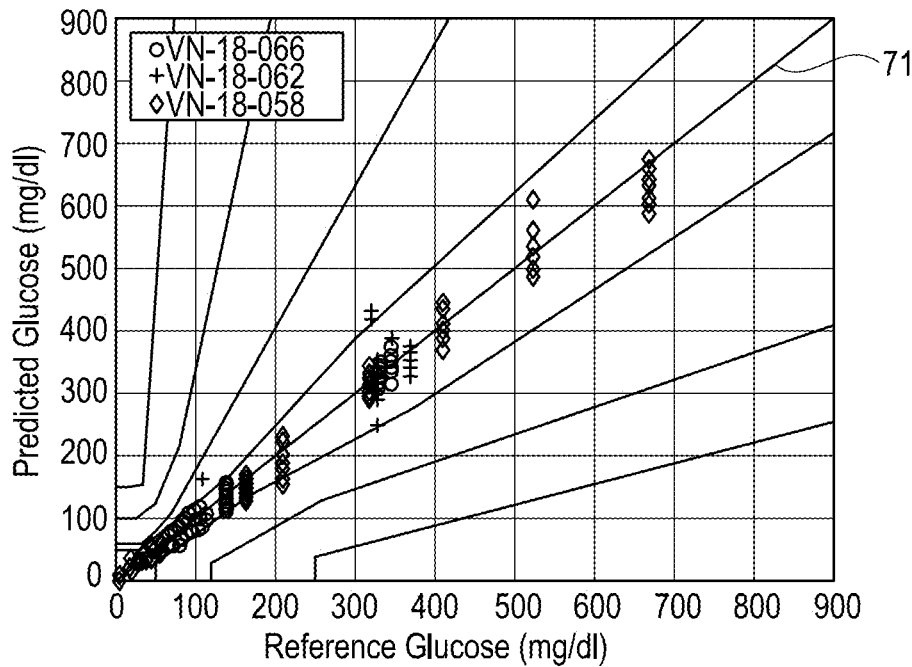
FIG. 7 shows a Parkes error grid illustrating the performance of the predicted blood glucose values versus actual blood glucose levels.
Figure 8:
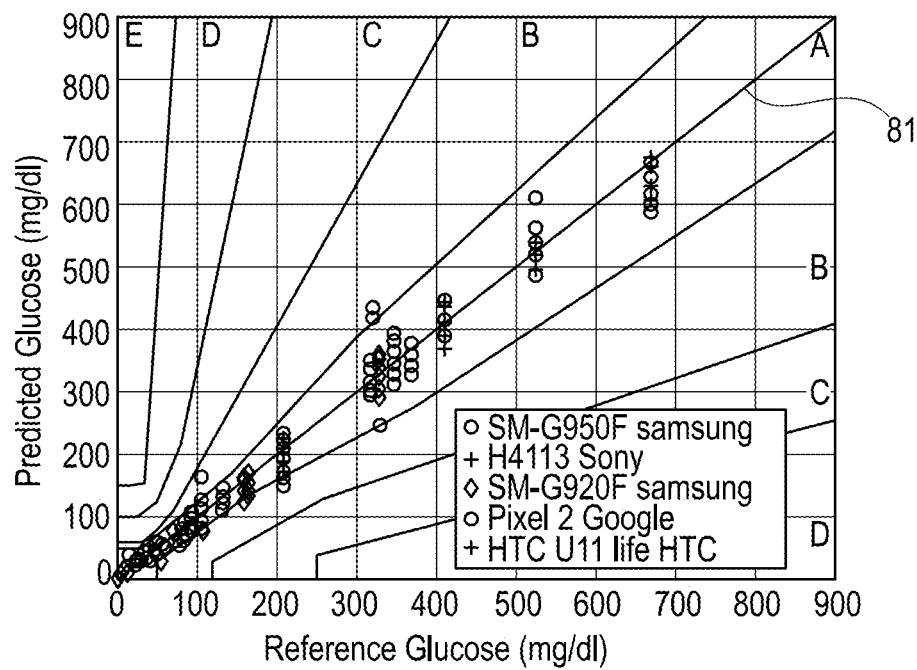
FIG. 8 shows another Parkes error grid illustrating the performance of the predicted blood glucose values versus actual blood glucose levels.

FIGS. 7 and 8 each show a Parkes error grid illustrating the performance of the determined blood glucose values versus actual blood glucose values on the full dataset. Parkes error grids (consensus error grids) are well-known graphical tools for comparing different data in quantitative diagnostics (Parkes et al., *Diabetes Care* 23: 1143-1148, 2000). Each y-axis corresponds to the predicted blood glucose values; each x-axis corresponds to the actual blood glucose values. Each error grid is divided into different zones A to D, corresponding to different error regions. Deviations from the bisecting lines 71, 81 within zone A correspond to low errors. It is desirable that most values are within zone A. Zone B corresponds to moderate errors, zone C to unacceptably large errors for the treatment of patients, and zone D to excessively large errors. In FIG. 7, different markers correspond to different experiment types; in FIG. 8, different markers correspond to different smartphone types. As can be seen from the FIGS. 7 and 8, the predicted blood glucose values correspond to the actual blood glucose values reasonably well for both different cell phone types and different experiment types.

Table 2 shows one example of how often blood glucose values fall into different Parkes error grid zones A to E for a traditional or non-ANN algorithm (parametric multivariate linear regression) in comparison with the ANN model approach. Values within the zones A and B are considered acceptable, values within the zones C to E unacceptable to critical. Both the traditional algorithm and the ANN model can be trained with coding datasets M1 and M2. Subsequently, unknown cell phone types (coding datasets M4, M5, and M6) can be assessed. The coding datasets M1 to M5 in this example stem from lab data determined under standard conditions (T=24° C., Hum=45%) at a standard measuring station and including a Hexokinase Glucose reference value. Environmental and handling effects can be minimized. Five different types of cell phones can be employed per coding dataset. Hence, training can be performed by use of 10 different cell phone types. The thus generated algorithms can be subsequently provided with unknown data of 3×5=15 different cell phone types.

TABLE 2

Comparison of traditional and ANN approaches for blood glucose prediction.

| Traditional algorithm | n | A | B | C | D | E |
|---|---|---|---|---|---|---|
| Coding set M1 | 371 | 338 (91.11%) | 33 (8.89%) | 0 | 0 | 0 |
| Coding set M2 | 470 | 405 (86.17%) | 65 (13.83%) | 0 | 0 | 0 |
| Coding sets M4, M5, M6 | 1429 | 1159 (81.11%) | 263 (18.40%) | 2 (0.14%) | 5 (0.35%) | 0 |
| ANN model | n | A | B | C | D | E |
| Coding set M1 | 371 | 362 (97.57%) | 9 (2.43%) | 0 | 0 | 0 |
| Coding set M2 | 470 | 435 (92.55%) | 35 (7.45%) | 0 | 0 | 0 |

TABLE 2-continued

Comparison of traditional and ANN approaches for blood glucose prediction.

| Coding sets M4, M5, M6 | 1429 | 1106 (77.40%) | 323 (22.60%) | 0 | 0 | 0 | 5 |

As can be seen from table 2, the ANN model performs better in estimating blood glucose values for unknown cell phone types than the traditional algorithm. Importantly, no values from the ANN model are within the unacceptable zones C to E, corresponding to gross misclassifications of the blood glucose levels.

Figure 9:
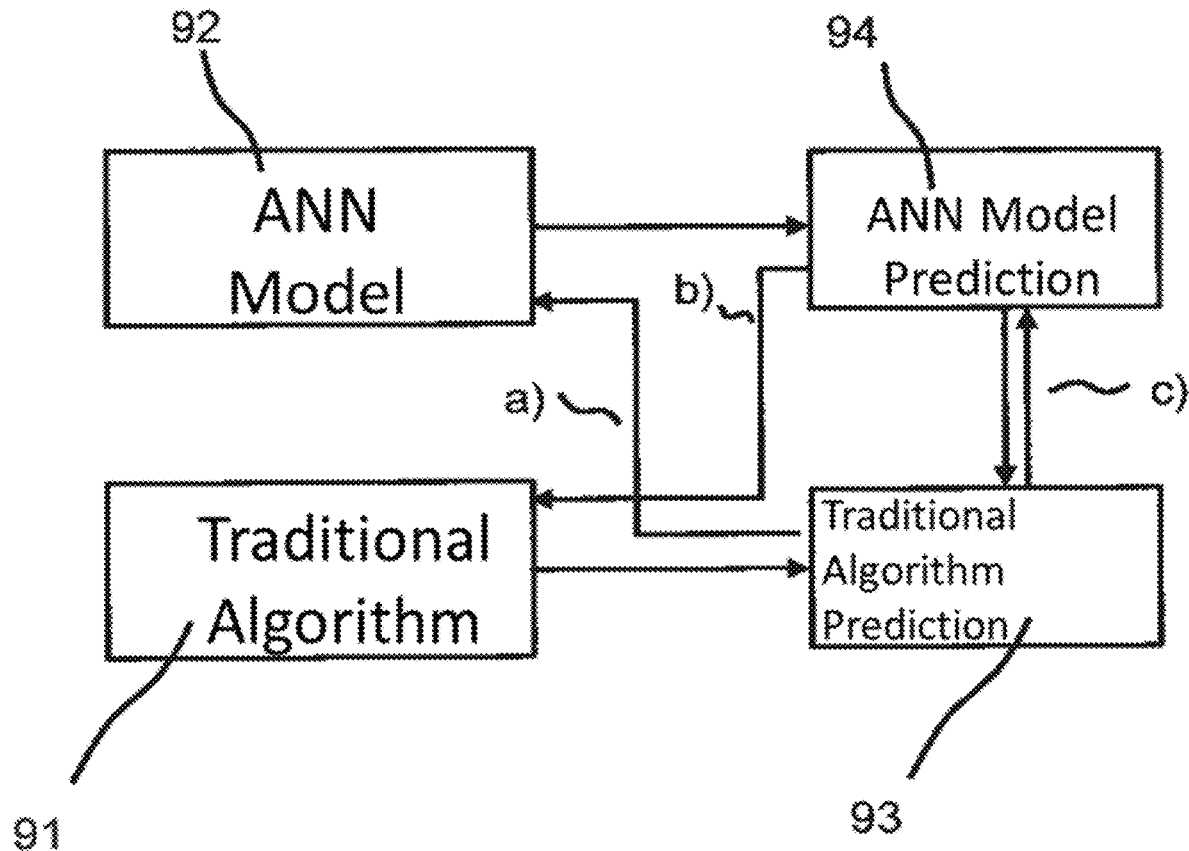
FIG. 9 shows a graphical representation of different types of combinations of traditional algorithms with ANN models.

In further examples for blood glucose prediction, a traditional algorithm 91 such as, e.g., polynomial fits can be used in combination with ANN models 92. FIG. 9 shows a graphical representation of different types of combinations that can be used:
  a) Predictions 93 from a traditional algorithm 91 can be used as an input (feature) to the ANN model 92;
  b) predictions 94 from an ANN model 92 can be used as an input to a traditional algorithm 91; and
  c) Both a traditional algorithm 91 and an ANN model 92 can be used and differences in the predictions 93, 94 from both algorithms can be used as a failsafe to eliminate incorrect predictions.

Figure 10:
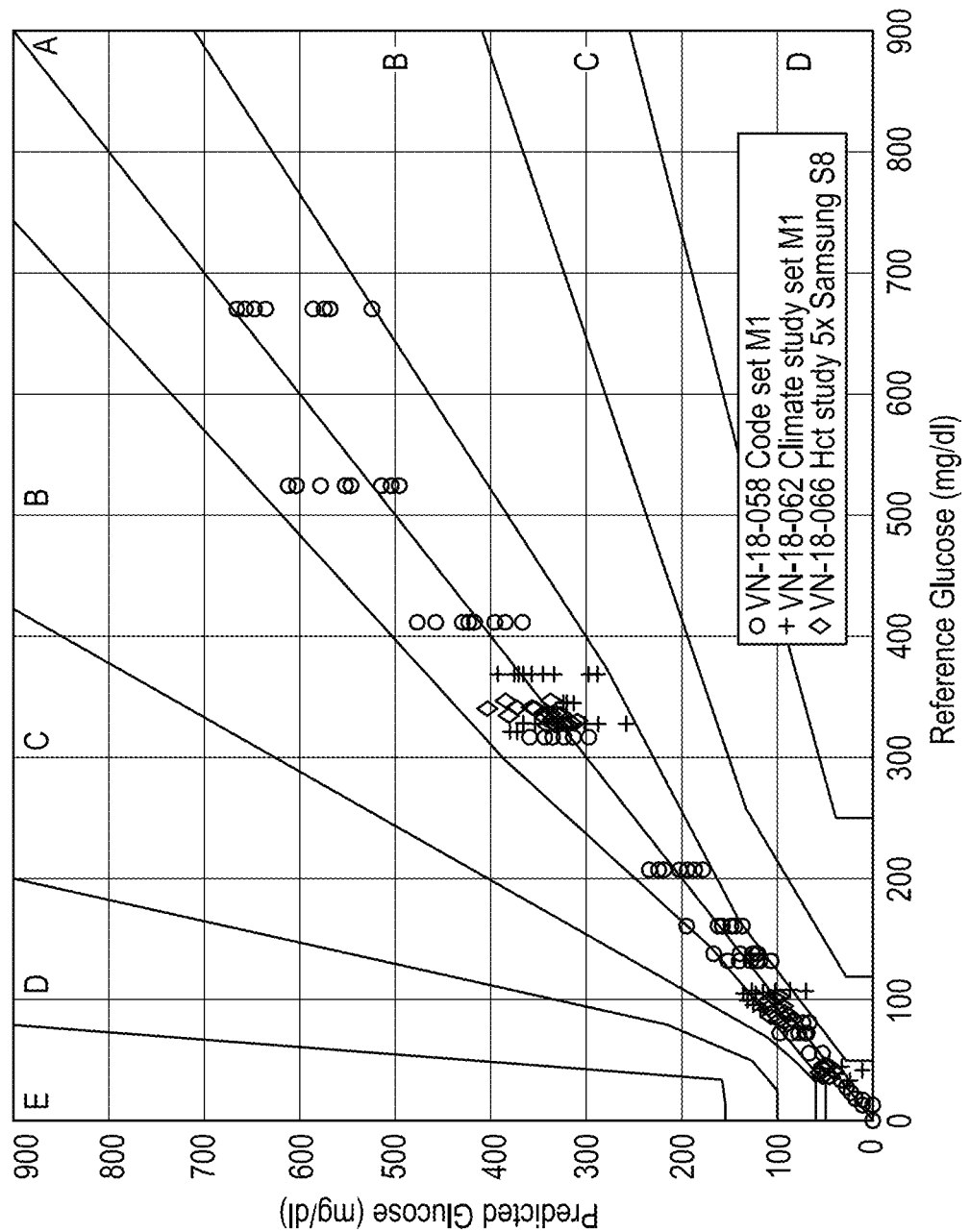
FIG. 10 shows a Parkes error grid depicting the predictions of an ANN model which uses traditional algorithm predictions as one of its inputs.

FIG. 10 shows a Parkes error grid depicting the predictions of the ANN model which uses traditional algorithm predictions as one of its inputs.

Figure 11:
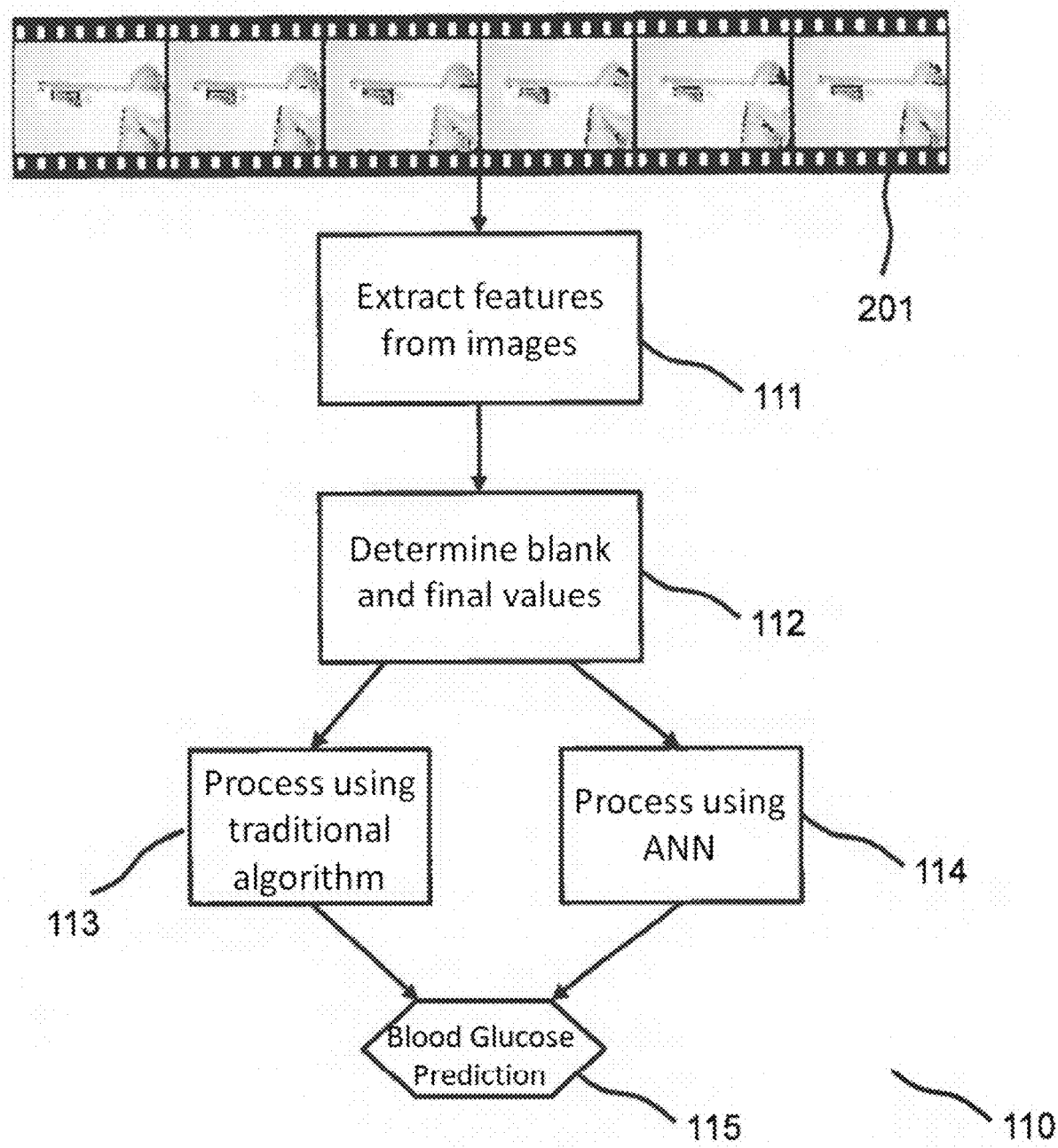
FIG. 11 shows a graphical representation of another embodiment of a combined traditional and ANN algorithm.

FIG. 11 shows a graphical representation of another embodiment of a combined traditional and ANN model algorithm 110. Out of the image series 201, including at least two images, certain features can be extracted (step 111). These features can then be monitored and a dry (blank) value and a final value can be determined using a kinetic algorithm (step 112).

The features are then processed in a traditional algorithm (step 113) and an ANN model (step 114) in parallel, resulting in blood glucose value predictions (step 115). Error flags can also be provided if applicable.

Figure 12B:
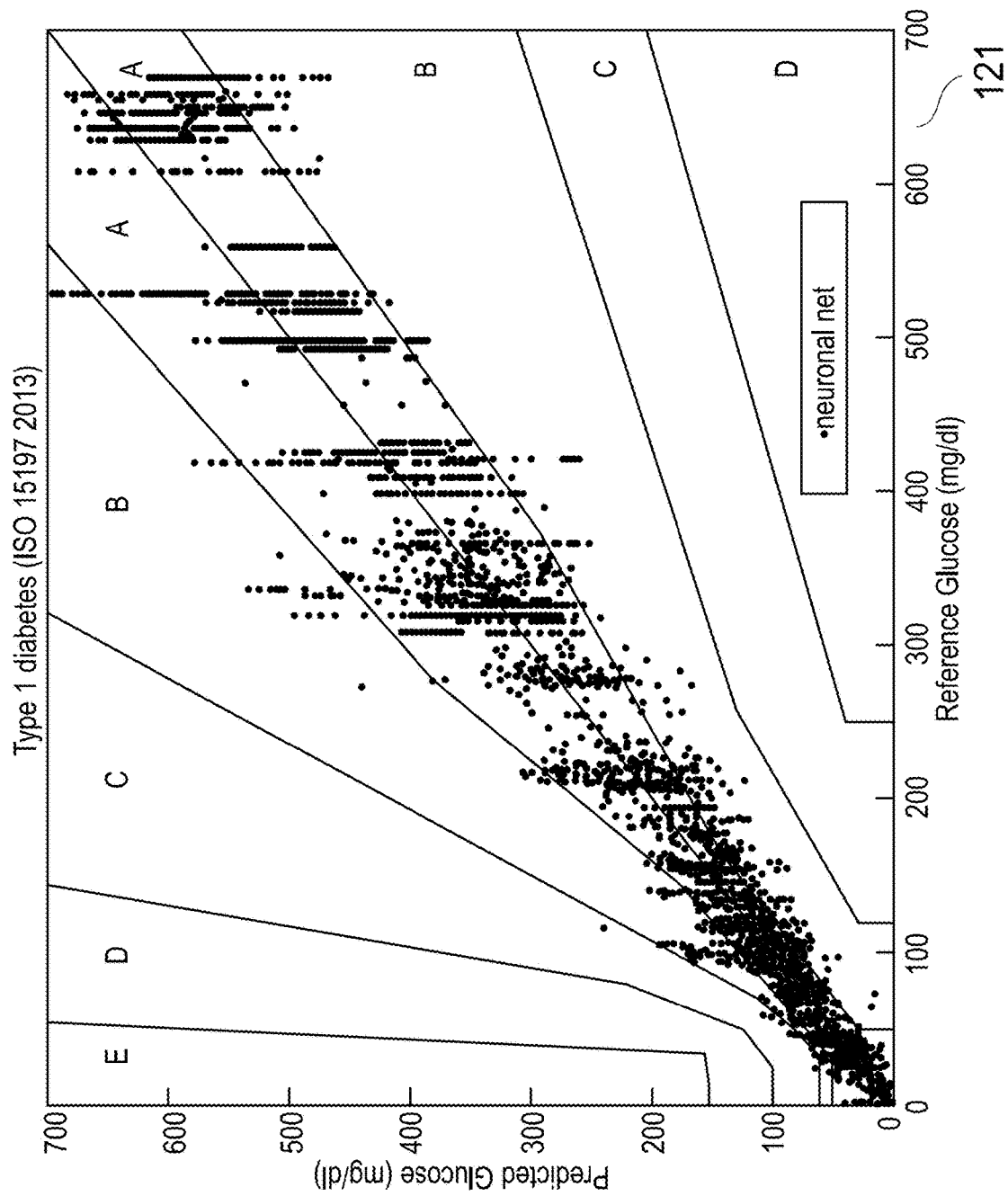
FIG. 12B shows a Parkes error grid for an ANN model.
Figure 12C:
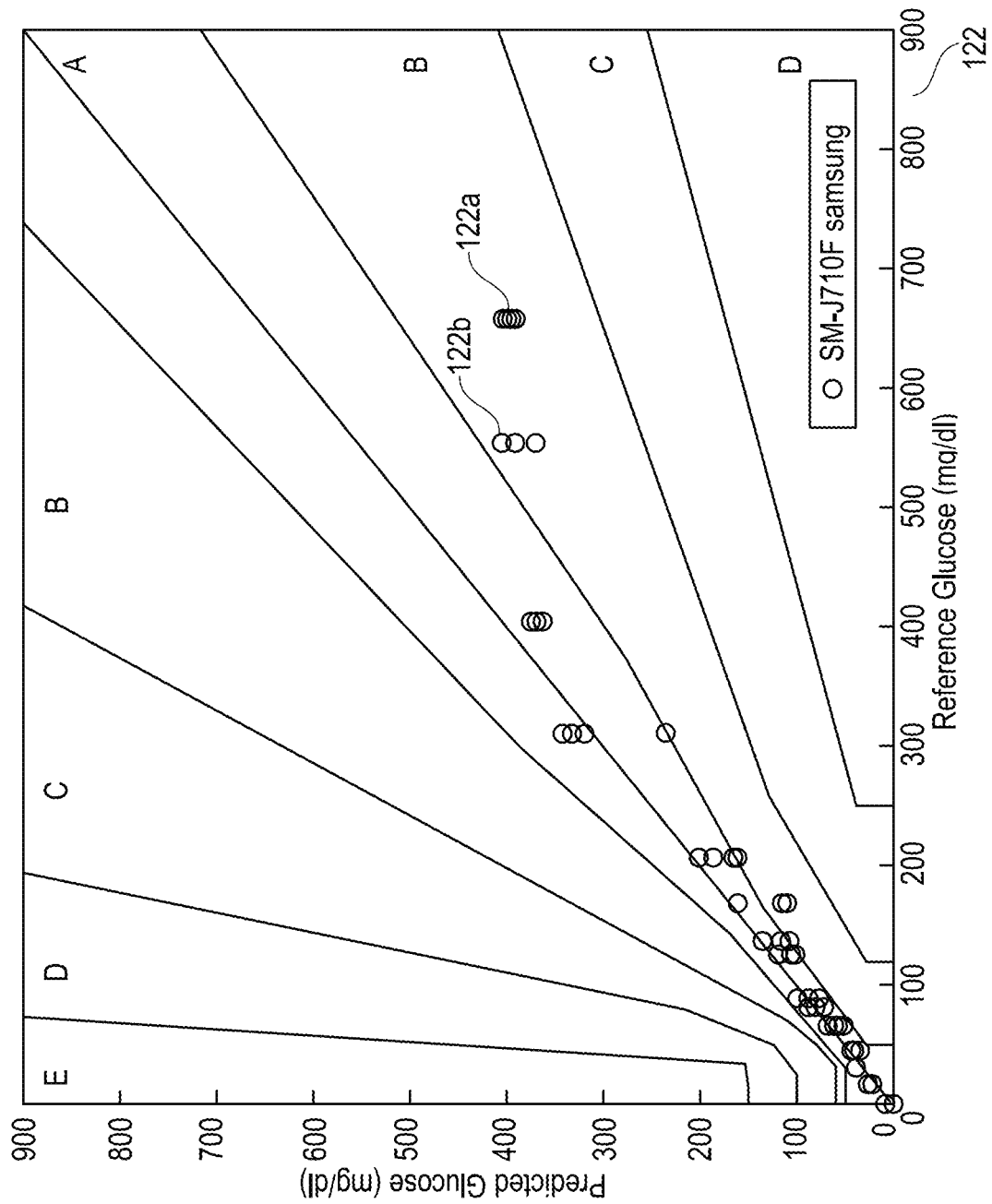
FIG. 12C shows a Parkes error grid for an ANN only trained on blood glucose values below 450 mg/dl.

FIGS. 12A, 12B and 12C show three Parkes error grids 120, 121, 122, respectively, for comparing the performance of traditional and ANN model approaches. For error grid 120, depicted in FIG. 12A, only a traditional algorithm was employed; for error grid 121, depicted in FIG. 12B, only an ANN model was employed. As can be seen in error grids 120 and 121, the measurement performance for the feature based ANN model is better than the one for the traditional algorithm. Error grid 122, depicted in FIG. 12C, demonstrates why not to only rely on ANN models. Here, as a showcase, the ANN was only trained on blood glucose values below 450 mg/dl. Therefore, samples 122a, 122b out of the training scope are severely misclassified. To protect against any unexpected input data entered into the ANN leading to wrong blood glucose results, the traditionally determined blood glucose values could be used as a failsafe for the ANN blood glucose results.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for determining concentration of an analyte in a sample of a body fluid, the method comprising:
  (a) generating a first set of measurement data by using a plurality of devices to record images of a color transformation of a region of interest of a first test strip in response to applying a fluid containing an analyte;
  (b) training a neural network model using training data selected from the first set of measurement data;
  (c) prompting a user to generate a second set of measurement data by recording images of a color transformation of a region of interest of a second test strip in response to applying a body fluid containing an analyte;
  (d) prompting the user to apply the trained neural network model of step (b) to determine concentration of the analyte on the second test strip of step (c).

2. The method according to claim 1, further comprising: using a second analyzing algorithm, different from the neural network model, to determine a first estimation value of the concentration of the analyte on the second test strip.

3. The method according to claim 2, wherein the first estimation value comprises a target range for the concentration of the analyte on the second test strip.

4. The method according to claim 2, wherein the concentration of the analyte on the second test strip is determined by averaging the first estimation value of claim 2 and a concentration value determined by the neural network model of step (b).

5. The method according to claim 1, wherein the first and/or second set of measurement data includes color information derived from consecutive images recorded over a measurement period of time for the region of interest of the first and/or second test strip.

6. The method according to claim 5, wherein the measurement period of time is from about 0.1 to about 1.5 s.

7. The method of claim 5, wherein the measurement period of time begins before the body fluid sample is applied to the test strip and ends after completion of the color change reaction.

8. The method according to claim 1, wherein the plurality of devices have different cameras and/or different image processing software.

9. The method according to claim 1, wherein the recorded images of the color transformation of the region of interest of the first test strip comprise images recorded with different optical image recording conditions.

10. The method according to claim 1, wherein the recorded images comprise images of the region of interest prior to applying the fluid containing an analyte to the region of interest.

11. The method according to claim 1, further comprising extracting image data from the recorded images for a blank region of the first test strip where no color transformation occurs.

12. The method according to claim 11, wherein the image data from the blank region of the first test strip is used to train the neural network model.

* * * * *